United States Patent [19]

Hashimoto

[11] 3,987,060

[45] Oct. 19, 1976

[54] DICYANOMETHYLENE-INDENO THIOPHENE AND DERIVATIVES

[75] Inventor: Mitsuru Hashimoto, Tokyo, Japan

[73] Assignee: Kabushiki Kaisha Ricoh, Tokyo, Japan

[22] Filed: Sept. 13, 1974

[21] Appl. No.: 505,729

Related U.S. Application Data

[62] Division of Ser. No. 425,967, Dec. 19, 1973, Pat. No. 3,871,883.

[30] Foreign Application Priority Data

Dec. 28, 1972 Japan .................................. 48-1944
Dec. 28, 1972 Japan .................................. 48-1945

[52] U.S. Cl. .............................................. 260/329 F
[51] Int. Cl.² ........................................ C07D 333/00
[58] Field of Search .................................. 260/329 F

[56] References Cited

OTHER PUBLICATIONS

MacDowell et al., "Chem. Abstracts," vol. 67, (1967), 64147u.

*Primary Examiner*—James O. Thomas, Jr.
*Assistant Examiner*—A. Siegel
*Attorney, Agent, or Firm*—Cooper, Dunham, Clark, Griffin & Moran

[57] ABSTRACT

Electrophotographic light-sensitive materials having a photoconductive layer formed on an electroconductive support, the photoconductive layer comprising an organic photoconductive compound (monomer or polymer) and 4-dicyanomethylene-4H-indeno[1,2-b]thiophene or 8-dicyanomethylene-8H-indeno[2,1-b]thiophene or their derivatives as sensitizers, and processes for preparing such compounds from 4H-indeno[1,2-b]thiophen-4-one or 8H-indeno[2,1-b]thiophen-8-one or their derivatives and malonitrile.

5 Claims, No Drawings

DICYANOMETHYLENE-INDENO THIOPHENE AND DERIVATIVES

RELATED APPLICATION

United States patent application Ser. No. 416,792 filed Nov. 19, 1973 now abandoned describes and claims the corresponding indenothiophenones which are starting materials for the compounds of this invention.

This is a division, of application Serial No. 425,967 filed Dec. 19, 1973, now U.S. Pat. No. 3,871,883.

BACKGROUND OF THE INVENTION

Electrophotographic light-sensitive materials comprise an electroconductive support with a photoconductive layer formed thereon. The principle of an electrophotographic process is that an electrostatic latent image is produced by image-wise exposure of a charged photoconductive layer and the image is then developed by a developer or toner (in liquid or powder form) which is electrically precipitated on the latent image to form a visible image. Conventionally, for forming the photoconductive layer, inorganic photoconductors such as photoconductive zinc oxide or selenium are used. Recently, the use of an organic photoconductive compound e.g. a photo conductive polymer such as poly-N-vinylcarbazole in place of the inorganic photoconductors has been proposed. Amongst the advantages of organic photoconductive compounds are transparency and mechanical flexibility. Additionally, they are easy to form into photoconductive layers. On the other hand, they absorb light in the ultraviolet region of the spectrum, but are not sensitive to visible light. To overcome this disadvantage, i.e. to shift their absorption into the visible region of the spectrum, dyestuff sensitizers are added to the organic photoconductive compounds. Such dyestuffs as have been previously employed are generally not stable and bleach out quickly so that the organic photoconductive compounds lose their sensitivity in the visible region. As a result, electrophotographic light-sensitive materials prepared utilizing organic photoconductive compounds containing dyestuff sensitizers are of limited practical use.

It is, therefore, an object of the present invention to provide stable sensitizers and improved electrophotographic light-sensitive materials containing such stable sensitizers.

SUMMARY OF THE INVENTION

The present invention relates to electrophotographic light-sensitive materials having a photoconductive layer formed on an electroconductive support, the photoconductive layer comprising an organic photoconductive compound such as a photoconductive monomer or polymer and 4-dicyanomethylene-4H-indeno[1,2-b]thiophene or 8-dicyanomethylene-8H-indeno[2,1-b]thiophene or their derivatives as a sensitizer, and a process of preparing such compounds and their derivatives.

In general, electrophotographic light-sensitive materials comprise an electroconductive support and a photoconductive layer formed on the support.

The electrophotographic light-sensitive materials of the present invention are characterized in that the photoconductive layer comprises an organic photoconductive compound sensitized with 4-dicyanomethylene-4H-indeno[1,2-b]thiophene or 8-dicyanomethylene-8H-indeno[2,1-b]thiophene and their derivatives having the following general formulas. These compounds are used as sensitizers for the organic photoconductive compound.

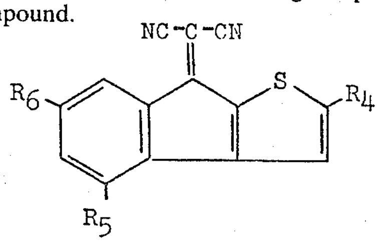

(A)

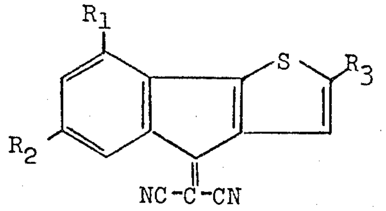

(B)

wherein $R_1$, $R_2$, $R_3$, $R_4$, $R_5$ and $R_6$ are hydrogen or nitro groups.

These compounds are respectively designated as follows:

A. 8-dicyanomethylene-8H-indeno[2,1-b] thiophene.

B. 4-dicyanomethylene-4H-indeno[1,2-b] thiophene.

The electrophotographic light-sensitive materials of the present invention may be prepared by forming a photoconductive layer on an electroconductive support, the photoconductive layer comprising any of a variety of organic photoconductive monomers such as N-vinylcarbazole or organic photoconductive polymers such as poly-N-vinylcarbazole and 4-dicyanomethylene-4H-indeno[1,2-b]thiophene or 8-dicyanomethylene-8H-indeno[2,1-b]thiophene or their derivatives as indicated above. 4-decyanomethylene-4H-indeno[1,2-b]thiophene or 8-dicyanomethylene-8H-indeno[2,1-b]thiophene or their derivatives are utilized in an amount of from 0.01 to 1.2 mole per mole of organic photoconductive monomer or per monomeric unit of the organic photoconductive polymer (1 mole of the organic photoconductive polymer is represented by monomeric unit of the polymer).

4-dicyanomethylene-4H-indeno[1,2-b]thiophene or 8-dicyanomethylene-8H-indeno[2,1-b]thiophene and its derivatives for use in accordance with the present invention are shown by structural formulas below:

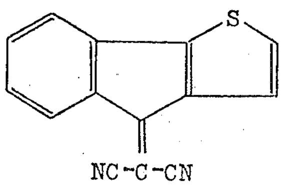

(I)

4-dicyanomethylene-4H-indeno-[1,2-b]thiophene

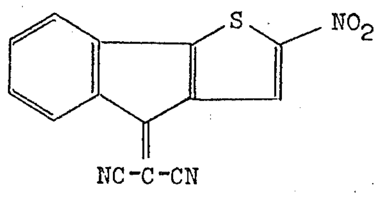

(II)

2-nitro-4-dicyanomethylene-4H-indeno[1,2-b]thiophene

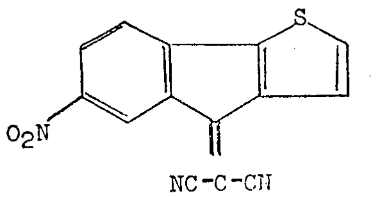
6-nitro-4-dicyanomethylene-4H-indeno[1,2-b]thiophene (III)
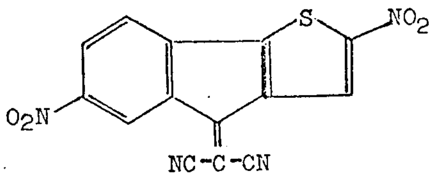
2,6-dinitro-4-dicyanomethylene-4H-indeno[1,2-b]thiophene (IV)
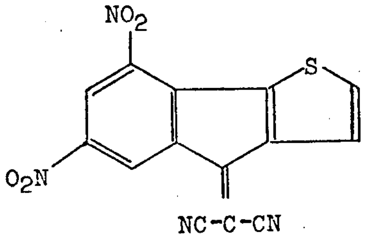
6,8-dinitro-4-dicyanomethylene-4H-indeno[1,2-b]thiophene (V)
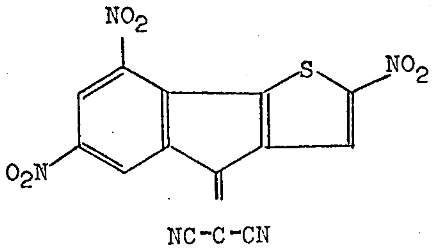
2,6,8-trinitro-4-dicyanomethylene-4H-indeno[1,2-b]thiophene (VI)
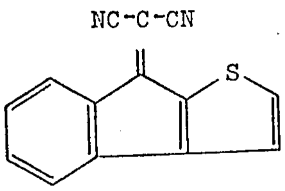
8-dicyanomethylene-8H-indeno-[2,1-b]thiophene (VII)

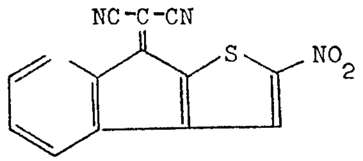
2-nitro-8-dicyanomethylene-8H-indeno-[2,1-b]thiophene (VIII)
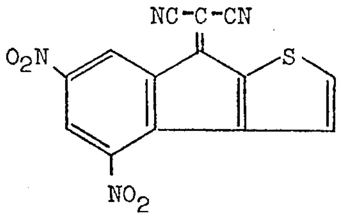
4,6-dinitro-8-dicyanomethylene-8H-indeno-[2,1-b]thiophene (IX)
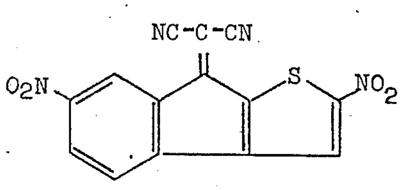
2,6-dinitro-8-dicyanomethylene-8H-indeno-[2,1-b]thiophene (X)
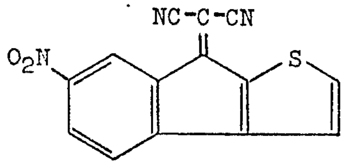
6-nitro-8-dicyanomethylene-8H-indeno-[2,1-b]thiophene (XI)
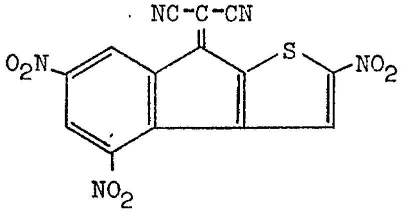
2,4,6-trinitro-8-dicyanomethylene-8H-indeno-[2,1-b]thiophene (XII)

Organic photoconductive compounds for use in accordance with the present invention include the following:

Preferred organic photoconductive polymers include poly-N-vinylcarbazole, chlorinated or brominated poly-N-vinylcarbazole, polyvinylpyrene, polyvinylnaphthalene, polyvinylanthracene, poly-9-vinylfluorene, poly-1-arylimidazole, bromopyrene-formaldehyde resin and poly-p-phenylene-1,3,4-oxadiazole.

Preferred organic photoconductive monomers include N-vinylcarbazole, N-ethylcarbazole, anthracene and pyrene.

However, poly-N-vinylcarbazole and chlorinated or brominated poly-N-vinylcarbazole are preferably used as an organic photoconductive compound.

Suitable electroconductive supports which may be used in the present invention include, for example, metallic sheets such as aluminium foil and synthetic resin sheets coated with a layer of aluminium.

Electrophotographic light-sensitive materials in accordance with the present invention can be produced, for example, as follows:

From about 0.01 to about 1 mole of 4-dicyanomethylene-4H-indeno[1,2-b]thiophene or 8-dicyanomethylene 8H-indeno[2,1-b]thiophene or their derivatives as shown above is mixed with 1 mole of the organic monomer or monomeric unit of the organic photoconductive polymer and the mixture is dissolved in an organic solvent such as tetrahydrofuran or dioxane to prepare a light-sensitive solution. Polyester resin, novolac resin or acrylic resin may, if desired, be added to this solution. Furthermore, polychlorobiphenyl may be added to this solution. The resulting light-sensitive solution is then applied to a surface of an electroconductive support, for example, using a doctor blade, left to set, and then dried.

The following Examples are given by way of illustration only.

EXAMPLE 1

A light-sensitive solution containing a photoconductive composition for use in the production of a photoconductive layer was prepared from the following ingredients:

| | |
|---|---|
| poly-N-vinylcarbazole | 387 mg (2m moles) |
| 6,8-dinitro-4-dicyanomethylene-4H-indeno[1,2-b]thiophene | 65 mg (0.2m mole) |
| Polyester Adhesive 49000 (Trade mark of polyester resin sold by E. I. Du Pont de Nemours & Co., Inc.) | 38 mg |

This light-sensitive solution was applied as a coat on an aluminium layer on a polyester resin film (thickness: 75 μ), using a doctor blade set at a 200 μ gap, and then dried in a desicator having silica gel to evaporate a solvent, and further dried at a temperature of 60° C for about 10 minutes and at a temperature of 120° C for about 2 minutes. A photoconductive layer having a thickness of about 7 μ was formed on the aluminium layer.

The sensitivity of the electrophotographic light-sensitive material (No. 1) of the present invention thus obtained was evaluated using "Electrostatic paper analyser Type SP-428 sold by Kawaguchi Denki Seisakusho" as follows:

The material obtained above was divided into two parts. The photoconductive layer was negatively or positively charged by a corona discharge of about −6kV or +6kV for 20 seconds to obtain a surface electric potential Vdo and then subjected to dark decay for 20 seconds to obtain a surface residual potential Vpo. This charged light-sensitive material was exposed to a tungsten filament lamp whose illuminance at the surface of the light-sensitive layer was adjusted to be 20 lux. The time (seconds) required to reduce the surface electric potential to one half or one fifth of the residual surface potential Vpo were measured. The amounts of exposure, $E_{1/2}$ (lux.sec) and $E_{1/5}$ (lux.sec), required to reduce the surface electric potential to one half and one fifth of Vpo are calculated by "20 lux × time (seconds)". The $E_{1/2}$ and $E_{1/5}$ represent the sensitivity of the electrophotographic light-sensitive material. The lower the value of $E_{1/2}$ or $E_{1/5}$ the higher the sensitivity of the light-sensitive material. The value of Vpo, $E_{1/2}$ and $E_{1/5}$ are shown in the Table 1 below.

Table 1

| Charge | Vpo (V) | $E_{1/2}$ (lux.sec) | $E_{1/5}$ (lux.sec) |
|---|---|---|---|
| − | 480 | 14.0 | 44.9 |
| + | 425 | 11.7 | 33.7 |

Similar results are obtained with the corresponding 8-dicyanomethylene-8H compound.

EXAMPLES 2 – 8

Electrophotographic light-sensitive materials (No. 2 – No. 8) of the present invention were obtained by repeating the same procedure as that of Example 1 except that organic photoconductive compound, sensitizer, Polyester Adhesive 49000 and tetrahydrofuran were used as shown in the following Table 2 and thickness of photoconductive layer was that as shown in the Table 2.

Table 2

| No. 2 | poly-N-vinyl-carbazole | 6,8-dinitro-4-dicyanomethyl-ene-4H-indeno [1,2-b]-thiophene | Polyester Adhesive 49000 | Tetra-hydro-furan | thick-ness of photo-conduc-tive layer |
|---|---|---|---|---|---|
| | 290 mg (1.5 m moles) | 243 mg (0.75 m mole) | 46 mg | 5.2 g | about 12 μ |

TABLE 2 – Continued

| | | | | | |
|---|---|---|---|---|---|
| No.3 | 1-bromopyrene formaldehyde resin | " | " | " | " |
| | 586 mg (2 m moles) | 65 mg (0.2 m mole) | 290 mg | 5.3 g | about 11 μ |
| No.4 | 586 mg (2 m moles) | 130 mg (0.4 m mole) | 324 mg | 3.9 g | about 11 μ |
| No.5 | poly-N-vinyl-carbazole | 2,6,8-trinitro-4-dicyanomethyl-ene-4H-indeno [1,2-b]-thiophene | " | " | " |
| | 387 mg (2 m moles) | 37 mg (0.1 m mole) | 37 mg | 6.1 g | about 4 μ |
| No.6 | 1-bromopyrene formaldehyde resin | " | " | " | " |
| | 586 mg (2 m moles) | 37 mg (0.1 m mole) | 280 mg | 5.1 g | about 10 μ |
| No.7 | *1) chlorinated poly-N-vinyl-carbazole | 6,8-dinitro-4-dicyanometh-ylene-4H-indeno[1,2-b]-thiophene | " | " | " |
| | 342 mg (1.5 m moles) | 243 mg (0.75 m mole) | 48 mg | 6.0 g | about 10 μ |
| No.8 | *2) brominated poly-N-vinyl-carbazole | " | " | " | " |
| | 348 mg (1.5 m moles) | 243 mg (0.75 m mole) | 49 mg | 6.0 g | about 10 μ |

*1)Chlorine is contained in a proportion of one chlorine atom per monomeric unit of poly-N-vinyl-carbazole.
*2)Bromine is contained in a proportion of one bromine atom per two monomeric units of poly-N-vinyl-carbazole.

Vpo, $E_{1/2}$ and $E_{1/5}$ of the light-sensitive materials No. 2 – No. 8 were measured by repeating the same procedure as that of Example 1. The values obtained are shown in the Table 3 below.

Table 3

| No. | Charge | Vpo (V) | $E_{1/2}$ (lux.sec) | $E_{1/5}$ (lux.sec) |
|---|---|---|---|---|
| 2 | – | 505 | 20.6 | 61.7 |
| | + | 340 | 24.0 | 68.6 |
| 3 | – | 1100 | 14.6 | 67.1 |
| | + | 800 | 23.7 | 75.5 |
| 4 | – | 880 | 26.9 | 86.9 |
| | + | 900 | 29.2 | 93.2 |
| 5 | – | 660 | 22.9 | 69.4 |
| | + | 560 | 14.9 | 47.7 |
| 6 | – | 420 | 32.0 | 81.0 |
| | + | 270 | 57.4 | 93.2 |
| 7 | – | 650 | 18.3 | 55.0 |
| | + | 490 | 22.5 | 60.1 |
| 8 | – | 630 | 19.9 | 60.0 |
| | + | 490 | 23.3 | 67.7 |

In the Examples supra, only 6,8-dinitro-4-dicyanomethylene-4H-indeno[1,2-b]thiophene (Formula V) and 2,6,8-trinitro-4-dicyanomethylene-4H-indeno[1,2-b]thiophene (Formula VI) were used as a sensitizer. However, the values of Vpo, $E_{1/2}$ and $E_{1/5}$ similar to those as shown in the Tables 1 and 3 can be obtained by using 4-dicyanomethylene-4H-indeno[1,2-b]thiophene or its derivatives as shown in Formulas I – IV in place of the above-mentioned two 4-dicyanomethylene-4H-indeno[1,2-b]thiophene derivatives in an amount of from 0.01 to 1 mole per monomeric unit of poly-N-vinylcarbazole, chlorinated or brominated poly-N-vinylcarbazole, or 1-bromopyrene formaldehyde resin.

Similar results are obtained with the corresponding 8-dicyanomethylene-8H compounds with the same compositions.

Electrophotographic light-sensitive materials having sensitivity to visible light can be produced with an organic photoconductive compound having no sensitivity to visible light by adding 4-dicyanomethylene-4H-indeno[1,2-b]thiophene or 8-dicyanomethylene-8H-indeno[2,1-b]thiophene or their derivatives to said organic photoconductive compounds.

The 4-dicyanomethylene-4H-indeno[1,2-b]thiophene compounds of this invention are novel.

Such 4-dicyanomethylene-4H-indeno[1,2-b]thiophene and its derivatives can be prepared by the process as described below.

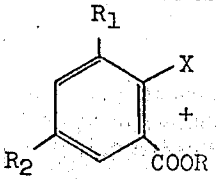

(1)

Benzoic acid ester derivative

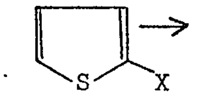

(2)

Thiophene derivative

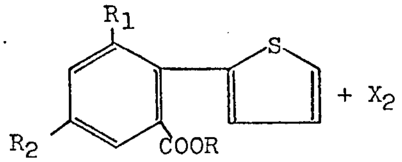

(3)

2-α-thienylbenzoic acid ester derivative wherein $R_1$ and $R_2$ are hydrogen or nitro, X is chlorine, bromin or iodine and R is a lower alkyl group of from one to four carbon atoms. The reaction as shown above is carried out in an organic solvent such as dimethylformamide at a temperature of from 50° C to 150° C.

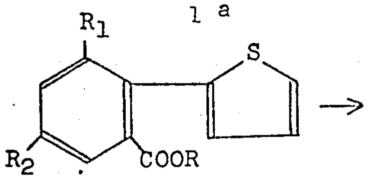

(3)

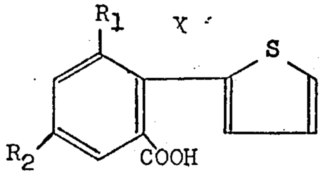

(4)

2-α-thienylbenzoic acid derivative wherein $R_1$, $R_2$ and R are same as mentioned above. The reaction as shown above is carried out in an aqueous solution of NaOH at a temperature of from 15° C to 60° C.

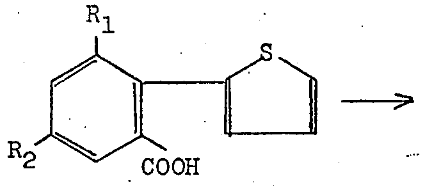

(4)

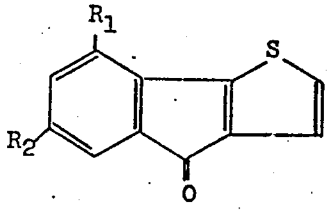

(5)

Indenothiophenone derivative the reaction of ring closure as shown above is carried out in the presence of polyphosphoric acid at a temperature of from 70° C to 150° C.

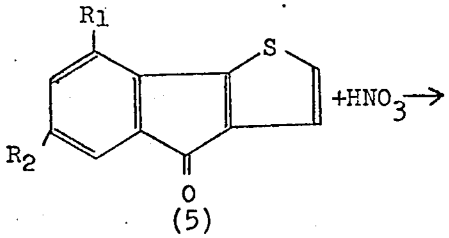

(5)

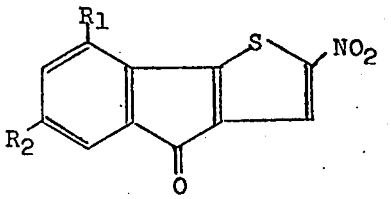

(6)

The nitration as shown above if it is carried out is effected in the presence of conc. $H_2SO_4$ at a temperature of from 0° C to 15° C.

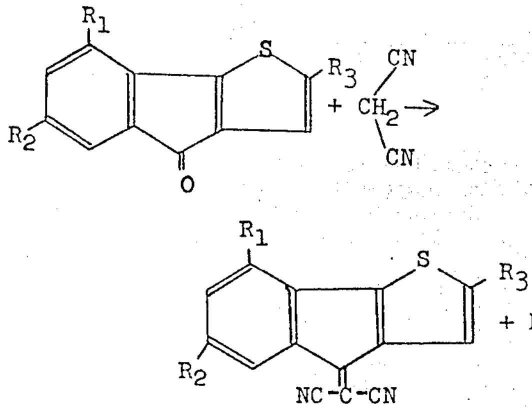

(5)

4-dicyanomethylene-4H-indeno[1,2-b]-thiophene or its derivatives (6)

The reaction as shown above is carried out in the presence of piperidine in a solution of tetrahydrofuran.

The novel compounds of formula 6 of the present invention as shown above is most useful as a sensitizer for organic photoconductive compounds such as poly-N-vinylcarbazole.

The processes of preparing 6,8-dinitro-4-dicyanomethylene-4H-indeno[1,2-b]thiophene and 2,6,8-trinitro-4-dicyanomethylene-4H-indeno[1,2-b]thiophene are shown in detail below:

13 g (0.05 mole) of methyl 2-chloro-3,5-dinitrobenzoate (m.p. 193° – 196° C, Formula 1 as shown above) and 21 g (0.1 mole) of 2-iodothiophene (b.p. 71° – 73° C at 16 mm Hg, Formula 2) were dissolved in 100 ml of dimethylformamide and the solution was heated at a temperature of 70° C. To this solution was added 20 g of active cupper powder (as prepared by the method disclosed in Journal of American Chemical Society Vol. 55 Page 4219 (1933) by E. C. Kleiderer and R. Adams) over 10 minutes and the solution was stirred at a temperature of about 70° C for 50 minutes. After the solution has been cooled, the reaction product was poured into 500 ml of cold water. The precipitate thus produced was filtered off and washed with water. After water was removed from the precipitate, the precipitate was added to 500 ml of acetone. After the stirring has been continued, the solution was filtered. The filtrate was treated with active carbon, and then filtered. The filtrate was condensed to obtain a crude product. 13.1 g of a yellowish crystalline product (m.p. 134° – 135° C) was obtained in an 85% yield by recrystallization of the crude product from ethyl alcohol. This product was identified to be methyl 2-α-thienyl-3,5-dinitrobenzoate (Formula 3) by ultimate analysis.

| Analysis: | C(%) | H(%) | N(%) | S(%) |
|---|---|---|---|---|
| Calculated for $C_{12}H_8N_2O_6S$ | 46.75 | 2.61 | 9.09 | 10.41 |
| Found | 46.86 | 2.60 | 9.02 | 10.61 |

The presence of carbonyl group was proved by infrared absorption spectrum at 1730 $cm^{-1}$.

23.6 g of methyl 2-α-thienyl-3,5-dinitrobenzoate (Formula 3) thus obtained was dissolved in 100 ml of dioxane and to this solution was added an aqueous solution of NaOH (6 g of NaOH in 200 ml of water) and the stirring was continued for 3 hours. To this solution was added a small amount of active carbon and the solution was filtered. To the filtrate was added a cold water and the filtrate was neutralized with 6H-HCl with cooling to obtain a yellowish crystalline product. The crystalline product was filtered off and washed with water, and then dried. A crude product (m.p. 171° – 172° C) was obtained in a yield of 21.5 g. A yellowish crystalline product (m.p. 172.5° – 173.5° C) was obtained by the recrystallization of the crude product from benzene. This product was identified to be 2-α-thienyl-3,5-dinitrobenzoic acid (Formula 4) by ultimate analysis.

| Analysis: | C(%) | H(%) | N(%) | S(%) |
|---|---|---|---|---|
| Calculated for $C_{11}H_6N_2O_6S$ | 44.90 | 2.06 | 9.52 | 10.90 |
| Found | 44.65 | 2.10 | 9.65 | 10.72 |

The presences of carbonyl group and hydroxyl group were respectively proved by infrared absorption spectrum at 1730 $cm^{-1}$ and 3000 $cm^{-1}$.

To 2 g of 2-α-thienyl-3,5-dinitrobenzoic acid (Formula 4) was added 60 g of polyphosphoric acid and the mixture was heated at a temperature of from 130° C to 140° C. After cooling, the reaction mixture was poured into 200 ml of cold water. The precipitate thus produced was filtered off and washed with an aqueous solution of sodium carbonate and water, and then dried. 18 g of a crude product (m.p. 206° – 207.5° C) was obtained in a 95% yield. An orange-brownish crystalline product (m.p. 209.5° – 210.0° C) was obtained by the recrystallization of the crude product from tetrahydrofuran. This product was identified to be a novel compound of 6,8-dinitro-4H-indeno[1,2-b]thiophen-4-one (Formula 5) by ultimate analysis.

| Analysis: | C(%) | H(%) | N(%) | S(%) |
|---|---|---|---|---|
| Calculated for $C_{11}H_4N_2O_5S$ | 47.83 | 1.46 | 10.11 | 11.61 |
| Found | 47.65 | 1.57 | 10.01 | 11.62 |

The presence of carbonyl group was proved by infrared absorption spectrum at 1730 $cm^{-1}$.

1.5 g 6,8-dinitro-4H-indeno[1,2-b]thiophen-4-one (Formula 5) was dissolved in 30 ml of conc. $H_2SO_4$ and to this solution was added drop-wise with stirring, 5 ml of $HNO_3$ (S.G. 1.38), at a temperature of from 5° C to 10° C, over 30 minutes. Stirring was continued at this temperature for 1.5 hours. This solution was poured into 200 ml of cold water. A yellowish crystalline product separated from the solution. The crude product was filtered and washed with water and then dried. 1.4 g of a yellowish needle-like crystalline product (m.p. 223° – 223.5° C) was obtained in an 80.5% yield by the recrystallization of the crude product from dioxane-ethyl alcohol. This product was identified to be a novel compound of 2,6,8-trinitro-4H-indeno[1,2-b]thiophen-4-one (Formula 6) by ultimate analysis.

| Analysis: | C(%) | H(%) | N(%) | S(%) |
|---|---|---|---|---|
| Calculated for $C_{11}H_3N_3O_7S$ | 41.16 | 0.93 | 13.08 | 9.98 |

-continued

| Analysis: | C(%) | H(%) | N(%) | S(%) |
|---|---|---|---|---|
| Found | 40.90 | 1.32 | 12.90 | 10.23 |

The presence of carbonyl group was proved by infrared absorption spectrum at 1730 $cm^{-1}$.

8g of 6,8-dinitro-4H-indeno[1,2-b]thiophen-4-one (Formula 5) and 3.8g of malonitrile were dissolved in 150ml of tetrahydrofuran and to this solution was added a few drops of piperidine under reflux. After the reflux was continued for 20 minutes, tetrahydrofuran was distilled off at reduced pressure. The residue was washed with methyl alcohol. 4.4g of 6,8-dinitro-4-dicyanomethylene-4H-indeno[1,2-b]thiophene (Formula V; m.p. 244° – 245.5° C) was obtained by recrystallization of the residue from dioxane.

| Analysis: | C(%) | H(%) | N(%) | S(%) |
|---|---|---|---|---|
| Calculated For $C_{14}H_4N_2O_4S$ | 51.85 | 1.24 | 17.28 | 9.89 |
| Found | 51.82 | 1.01 | 17.62 | 9.80 |

The presence of cyano group was proved by infrared absorption spectrum at $2230^{-1}$.

10g of 2,6,8-trinitro-4H-indeno[1,2-b]thiophen-4-one (Formula 6) and 4g of malonitrile were dissolved in a mixture of 200 ml of tetrahydrofuran and 200 ml of methyl alcohol and to this solution was added a few drops of piperidine under reflux. After the reflux was continued for 20 minutes, the crystals separated from the solution were filtered. After the crystals have been recrystallized from a mixture of dioxane and acetonitrile, 8g of 2,6,8-trinitro-4-dicyanomethylene-4H-indeno[1,2-b]thiophene (Formula VI; m.p. over 300° C) was obtained in the form of red plate crystal.

| Analysis: | C(%) | H(%) | N(%) | S(%) |
|---|---|---|---|---|
| Calculated for $C_{14}H_3N_5O_6S$ | 45.33 | 0.82 | 18.97 | 8.68 |

-continued

| Analysis: | C(%) | H(%) | N(%) | S(%) |
|---|---|---|---|---|
| Found | 45.85 | 0.84 | 19.04 | 9.02 |

The presence of cyano group was proved by infrared absorption spectrum at 2220 $cm^{-1}$.

The corresponding 8-dicyanomethylene-8H compounds are also novel. They are prepared by the reaction of malononitrile on the corresponding 8H-indeno[2,1-b]thiophene-8-ones as illustrated above. The starting materials are prepared by the procedures described in:

MacDowell et al; J. Org. Chem. 32, 2441 (1967) Dubard et al; Academy Science Ser. C. 271 (4) 311 (1970).

What is claimed is:

1. A compound of the formula:

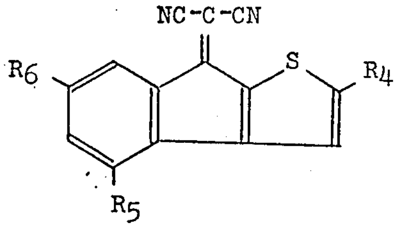

(A)

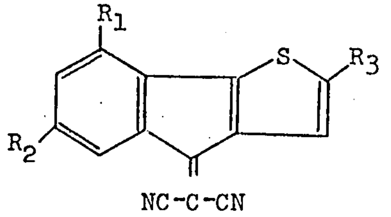

(B)

wherein $R_1$, $R_2$, $R_3$, $R_4$, $R_5$ and $R_6$ are hydrogen or nitro groups.

2. 6,8-Dinitro-4-dicyanomethylene-4H-indeno[1,2-b]thiophene.

3. 2,6,8-Trinitro-4-dicyanomethylene-4H-indeno[1,2-b]thiophene.

4. 2,6-Dinitro-8-dicyanomethylene-8H-indeno[2,1-b]thiophene.

5. 2,4,6-Trinitro-8-dicyanomethylene-8H-indeno[2,1-b]thiophene.

* * * * *